United States Patent [19]
Jang et al.

[11] Patent Number: 6,118,843
[45] Date of Patent: Sep. 12, 2000

[54] QUANTITATIVE STEREOSCOPIC RADIOGRAPHY METHOD

[75] Inventors: Bor Z. Jang; Wen-Chiang Huang, both of Auburn, Ala.

[73] Assignee: NANOTEK Instruments, Inc., Opelika, Ala.

[21] Appl. No.: 09/169,828

[22] Filed: Oct. 10, 1998

[51] Int. Cl.$^7$ .................................................. H04N 5/32
[52] U.S. Cl. ........................... 378/41; 378/42; 378/98.2; 348/51
[58] Field of Search ............................. 378/41, 42, 98.2; 348/51, 52, 53

[56] References Cited

U.S. PATENT DOCUMENTS

| | | |
|---|---|---|
| 1,447,399 | 3/1923 | Pease . |
| 1,992,894 | 2/1935 | Wantz . |
| 2,029,300 | 2/1936 | Arfsten . |
| 2,046,543 | 7/1936 | Boldingh . |
| 2,208,215 | 7/1940 | Gonzalez-Rincones . |
| 2,468,963 | 5/1949 | Dudley . |
| 2,511,097 | 6/1950 | Bonnet . |
| 2,518,884 | 8/1950 | Guentner et al. . |
| 2,521,154 | 9/1950 | Dudley . |
| 2,712,608 | 7/1955 | Atwell . |
| 3,004,159 | 10/1961 | Brancaccio . |
| 3,244,878 | 4/1966 | Stein et al. . |
| 3,382,362 | 5/1968 | Tokuyama et al. . |
| 3,560,740 | 2/1971 | Tripp ........................................... 250/61 |
| 3,671,745 | 6/1972 | Fouquart .................................... 250/61 |
| 3,783,282 | 1/1974 | Hoppenstein ............................. 250/313 |
| 3,984,684 | 10/1976 | Winnek .................................... 250/313 |
| 4,214,267 | 7/1980 | Roese et al. ............................. 358/111 |
| 4,696,022 | 9/1987 | Sashin et al. ............................. 378/41 |
| 4,737,972 | 4/1988 | Schoolman ................................ 378/41 |
| 4,769,701 | 9/1988 | Sklebitz .................................. 358/111 |
| 4,819,255 | 4/1989 | Sato .......................................... 378/42 |
| 5,073,914 | 12/1991 | Asahina et al. ............................ 378/42 |
| 5,090,038 | 2/1992 | Asahina .................................... 378/41 |
| 5,155,750 | 10/1992 | Klynn et al. .............................. 378/42 |
| 5,233,639 | 8/1993 | Marks ........................................ 378/41 |
| 5,493,595 | 2/1996 | Schoolman ................................ 378/41 |
| 5,818,064 | 10/1998 | Kohgami et al. .......................... 378/41 |
| 6,031,565 | 2/2000 | Getty et al. ............................... 348/51 |

OTHER PUBLICATIONS

F. H. Liu, et al. "Design and Test of a Stereoscopic X–Radiographic Observing & Measuring Instrument" International J. Pressure Vessels & Piping vol. 44 (1990) 353–364.

F. H. Liu, et al. "3–D Flaw Detection for the Welded Seams of Pressure Vessels", International J. Pressure Vessels & Piping vol. 48 (1991) 331–341.

*Primary Examiner*—David P. Porta
*Assistant Examiner*—Drew A. Dunn

[57] ABSTRACT

A method for stereoscopically displaying radiographic images of the internal structure of an object and determining the spatial coordinates of a selected feature image inside the object, including the steps of (a) producing a pair of left and right radiographic images on the same object at slightly different angles, (b) using image display means to present the two images, (c) using two distinct optical paths with two reference lines to permit viewing of the left image by the left eye and the right image by the right eye of an observer independently and simultaneously, and (d) performing and measuring horizontal shifting motions of the two images and obtaining the coordinates ($X_{GA}, Y_{GA}, Z_{GA}$) of an internal feature A with respect to a marker G according to a specified procedure. The procedure begins with aligning the image points of the marker G with their respective reference lines. Preferably, the same procedure is followed again for a second marker. The next step involves aiming and aligning the image points of the internal feature with respect to their respective reference lines. These procedures are carried out to allow for more convenient and accurate measurements of various image parallax values, which are in turn used to precisely calculate the location of an internal feature image of interest, such as a structural defect.

8 Claims, 9 Drawing Sheets

QUANTITATIVE STEREOSCOPIC RADIOGRAPHY METHOD

FIELD OF THE INVENTION

The present invention relates to improved stereo spectroscopic radiography methods and, more particularly, to methods for stereoscopically displaying radiographic images and quantitatively assessing the internal features of an object.

BACKGROUND OF THE INVENTION

High-energy radiations such as X-rays, gamma rays and neutrons are commonly used for non-destructive evaluation (NDE) of the internal defects of an object or for examination of the anomalies inside a human body. Radiographic images for either industrial NDE or medical applications can be obtained by radiography-on-film, fluoroscopy, and tomography methods. Each method has its advantages and disadvantages for a specific application.

Film radiography involves producing a sharp, natural size, permanent image of the internal features (e.g. flaws or anomalies) in an object. Such an image is usually not difficult to interpret. However, film radiography is often relatively slow and expensive.

Fluoroscopy or radioscopy entails the conversion of X-ray intensities into light intensities by utilizing a fluorescent screen. By placing the screen in the X-ray beam behind the specimen, one can produce an image of the specimen on the screen. The high X-ray absorbing capability of selected materials could result in low brightness images and hence poor sensitivity. One method to improve the fluoroscopic performance is to use a closed-circuit television (CCTV) camera to transfer the image on the fluorescent conversion screen on to a display monitor, relying on the electronic circuitry to enhance the signal and produce a bright image. Another technique is to use an image intensifier tube to convert X-rays into photons, which are then picked up by an image sensor. Commonly used image sensors are tube type TV cameras such as isocon, vidicons, and solid state charge coupled device (CCD) cameras. Another type of image sensor is the linear diode array (LDA), which can digitize and store the image to be viewd on a TV monitor. The digitization of the television signal has allowed a computer to be built into the system, and this advancement has greatly improved the attainable image quality. This development has also made it possible to perform real-time radiography.

Both the conventional film radiography and fluoroscopy only provide a two-dimensional (2-D) view of an object. In industrial applications, a 2-D image does not give a NDE technician an adequate perspective view on the spatial distribution of multiple flaws in a structural component, nor does it allow the technician to determine the depth of a particular flaw. For medical uses, a 2-D image may not provide a diagnostician adequate information as to the extent of a particular disorder, such as the exact depth of a foreign object in a human body.

To overcome some of the drawbacks of 2-D radiography, the approach of tomography was developed. Computed tomography (CT) involves obtaining and stacking a sequence of images representing 2-D cross sections or "slices" of the object. The 2-D images are acquired by rotating a thin, fan shaped beam of X-ray about the long axis of the object. X-ray attenuation measurements are obtained from many different directions across each slice. The 2-D images are reconstructed from these data through a sophisticated mathematical convolution and back projection procedure. A major drawback of tomography is that a NDE technician or diagnostician must mentally "stack" an entire series of 2-D slices in order to infer the structure of a 3-D object. The interpretation of a series of stacked 2-D images by an observer requires a great deal of specialized knowledge and skill. Further, such an approach is extremely time consuming and is prone to inaccuracy. The market price of a CT system typically exceeds a million U.S. dollars and, therefore, only select large hospitals or highly specialized governmental or industrial facilities could afford to have a CT system. Clearly, a need exists to develop a more affordable stereography system for 3-D inspection of the internal structure of an object.

Three-dimensional (3-D) or stereoscopic viewing provides a means for showing actual, more understandable spatial relationships among various features or flaws inside a body. Stereoscopic radiology was first introduced near the turn of the century, e.g. L. W. Pease, U.S. Pat. No. 1,447,399 (1923). Extensive patent and open literature can be found that describes the methods or apparatus for producing stereoscopic radiographs. U.S. Pat. No. 5,233,639 (1993), issued to Marks, summarized the pros and cons of various stereoscopic radiography methods, including stereo film radiography and stereoscopic fluoroscopy.

Most of the techniques that have been used to achieve the stereo effect is based on the theory of parallax. Specifically, an image recorded from the perspective of the right eye must be seen by the right eye while an image recorded from the perspective of the left eye must be seen by the left eye. A simple way to accomplish this is to provide distinct and separate optical paths to each eye from each recorded image. For instance, the right and left eye image pairs may be recorded as transparencies which, when inserted in a common hand-held 3-D viewer, are presented to each eye separately through magnifying lenses. A second example using the principle of distinct and separate optical paths is the mirror based viewer system. In this system, the image pairs are positioned under a viewer which, through two pairs of angled mirrors, directs each image to its corresponding observing eye. These conventional 3-D viewers, normally without proper markers or references, do provide the observer a 3-D perspective. However, they do not readily permit determination of the specific depths in which certain features (or flaws) are located relative to a predetermined reference.

Disclosed in U.S. Pat. No. 3,984,684 (1976) is a technique that allows both production of the stereo effect and measurements of the depth and size of one or more internal parts of an object. The technique entails successively directing the X-ray beams from an X-ray tube through the object, then through a parallax grating, and finally onto the film. The grating is mounted on the film support system. The object and the film support system together are translated in parallel paths laterally with respect to the beam path at different speeds. These speeds are such that the film and the object are maintained in congruent alignment with the X-ray tube. The grating moves slightly out of congruency causing the beam passing through the grating to slightly scan the film during the transverse. Also, the angle at which the object is exposed to radiation from the X-ray tube gradually changes. The film image contains a series of side-by-side variable aspect views or images of the object, corresponding in number to the number of slits in the grating. These images when viewed with a lenticular screen produce a 3-D perception. This technique requires the utilization of a complicated radiograph-taking system and a lenticular screen as described above. The stringent congruent alignment requirement has made this technique not readily adaptable to existing X-ray radiography apparatus.

Liu and co-workers (International Journal of Pressure Vessels & Piping, Vol.44, 1990, pp.353–364 and Vol.48, 1991, pp.331–341) have proposed a quantitative stereoscopic method which not only provides a 3-D perspective view of the internal features but permits convenient calculations of the coordinates (X,Y,Z) of one or more flaws inside an object. The method begins with taking a pair of radiograph films with the X-ray tube shifted laterally in a plane parallel to the film between the two exposures (while the object remains stationary). Alternatively, the same result can be achieved by shifting the object laterally while the X-ray source remains fixed. These radiograph films are then examined in a stereoscopic viewer. With a suitable marker placed on the specimen surface when the radiographic films are being exposed, the position of a defect image inside the specimen can be determined. Hitherto, very few industrial stereo radiographs have yielded very good results possibly because of the lack of reference detail and the incapability of the conventional stereoscopes in coping with films of the density used in industrial radiology. The method proposed by Liu, et al. provides a sound basis upon which more effective stereoscopes for quantitative radiography can be designed. This method, however, has been limited to film radiography. What is clearly needed is an improved method, which is based on Liu's principle and the various positive attributes of fluoroscopy, for conducting quantitative stereo radiology. The present invention has come about by following this line of thinking to develop methods for quantitative stereoscopic radiology.

OBJECTS OF THE INVENTION

The principal objects of the present invention are:

(1) to provide an improved method of stereoscopically displaying radiography images and allow for more convenient and accurate determination of the location of an internal feature.
(2) to provide an improved method for not only stereoscopic viewing of the internal defect dispersion of an object through radiographic films but also quantitative determination of the location of a defect inside an object.
(3) to provide an improved method for stereoscopic viewing of radiographic images displayed on TV or computer monitor screens and for determining the location of an internal feature.

SUMMARY OF THE INVENTION

The present invention provides methods for conducting quantitative stereoscopic radiography. These methods involve integrating the improved version of the abovementioned Liu's method of stereo film radiology with the great electronic imaging capabilities commonly associated with fluoroscopy.

Specifically, in one preferred embodiment, a method is disclosed which involves displaying a pair of radiographic images on the corresponding right and left video display devices of a stereoscopic viewing system. The pair of images can be obtained by transferring (e.g., scanning or digitizing) the corresponding radiography transparencies (negatives) or opaque prints onto one cathode ray tube (CRT), or two separate CRT monitors by using a common image scanner or TV camera. Alternatively, the images can be obtained by directly using common fluoroscopy devices to display the images without going through the intermediate film-taking procedure. This can be accomplished by directing the beam of an X-ray source (or other types of high energy radiation) through an object and by using an image intensifier to convert the radiation into visible light, allowing the image to be shown on a fluorescent screen. Alternatively, the light photons emitted from the image intensifier may be recorded by an image sensor which delivers the images either directly to video display devices or to an image storage device. In the latter case, the images will be later played back to the video display devices for examination.

As an example, referring to FIG. 1, both the right and left video display devices are each provided with a vertical reference line, which can be simply a thin opaque wire attached vertically (herein referred to as transversely, or in the Y-coordinate direction) to the display screen. Proper movement means are provided to allow the two images to be shifted laterally (horizontally, in the X-coordinate direction) either simultaneously in congruency or with respect to each other. Provisions are also given to record these shift distances. Shifting of the two images can be accomplished by positioning the two display devices on a slidable platform, hereinafter referred to as the primary platform, and then horizontally translating this platform. Either the left or the right display device is also supported on a secondary platform which is capable of moving horizontally, independent from the movement of the primary platform. The secondary platform is slidably attached to the top surface of the primary platform. The movements of both platforms can be recorded by any movement-measuring means such as a micrometer, sliding caliper, optical encoder, or any other type of displacement sensor. These measuring means are used to measure out the shift distances of both marker and defect images.

It may be noted that, by referring to FIG. 1 again, the X-coordinate direction is the X-ray source shifting direction (when the radiography image is taken), which is also parallel to the platform movement direction. The transverse direction on the image plane is the Y-coordinate direction, which is the vertical direction in FIG. 1. The Z-coordinate direction is perpendicular to both the X-direction and Y-direction; i.e. being normal to the image plane and substantially in the sample depth direction.

In another embodiment, the pair of radiography images may be shown side by side on the same display unit, such as a TV monitor or a computer monitor. The monitor screen is artificially divided into two zones: a left zone showing the image to be presented to the left eye and a right zone showing the image to be presented to the right eye of an observer. Vertically across each zone is one of the aforementioned reference lines or wires. There exist commercially available image processing software-hardware packages that are capable of providing and measuring the concurrent and separate movements of the two images on a TV screen or computer monitor. In yet another embodiment, the monitor is mounted on a horizontally slidable primary platform, which provides simultaneous shifting of the two images. Shifting of one image with respect to the other can be executed on the monitor by a simple computer command.

The two images can be viewed by an optical observing unit which is composed of two optical paths, one for observing the left image by the left eye and the other for observing the right image by the right eye of an observer. Each optical path begins with an objective lens that is capable of seeing a broad image area and directing the image to a pair of angled mirrors or prisms. The mirrors or prisms in turn send the image through an eyepiece into one eye of the observer. The separation between the two eyepieces is adjustable to suit different observers. The separation between the two objective lenses is designed to be in accord with the dimensions of, and the separation between the two images to ensure a broad viewing field. This pair of optical paths preferably are provided with a vertical movement means which is in turn supported by a sturdy stand. This vertical movement provision permits the observer to cover a wider viewing area in cases the display screen is wider than the range covered by the pair of objective lenses when in one specific height.

In summary, the present invention discloses improved methods for stereoscopically displaying radiographic images of the internal structure of an object and for determining the spatial coordinates of selected feature images inside the object. The method is composed of several steps:

(a) producing a pair of images on the same object taken from slightly different angles with image reference markers being placed on specified positions of the top or bottom surface of the object when irradiated; (b) using image display devices to present this pair of images with the two images being set up in a definitive orientation so that when the images are being viewed with both eyes by an observer, the two lines of sight connecting the eye balls and the corresponding image points of the image pair intersect; the two images being respectively provided with two stationary, transversely aligned reference lines across the image plane in the Y-direction; (c) using two distinct optical paths to permit viewing of the left image by the left eye and the right image by the right eye independently, as well as viewing of the images with both eyes simultaneously; (d) performing and measuring horizontal shifting motions of the two images according to a sequence of procedures to be specified at a later section. These procedures basically involve aiming and aligning the image points of an internal feature with their respective reference lines. The same procedures are then repeated to align the image points of a marker with their respective reference lines. Preferably, the same procedures are followed again for a second marker. These procedures are carried out to allow for more convenient and accurate measurements of various image parallax values, which are in turn used to precisely calculate the location of an internal feature image of interest.

DETAILED DESCRIPTION OF THE PREFERRED EMBODIMENTS

As required, detailed embodiments of the present invention are disclosed herein. The described embodiments are to be understood as merely exemplary of the invention, which may be embodied in various forms. Therefore, specific structural and functional details disclosed herein are not to be construed as limiting, but merely as a basis for the claims and as a representative basis for teaching those who are skilled in the art to variously employ the present invention for a wide range of appropriately detailed structures.

Figure 1:
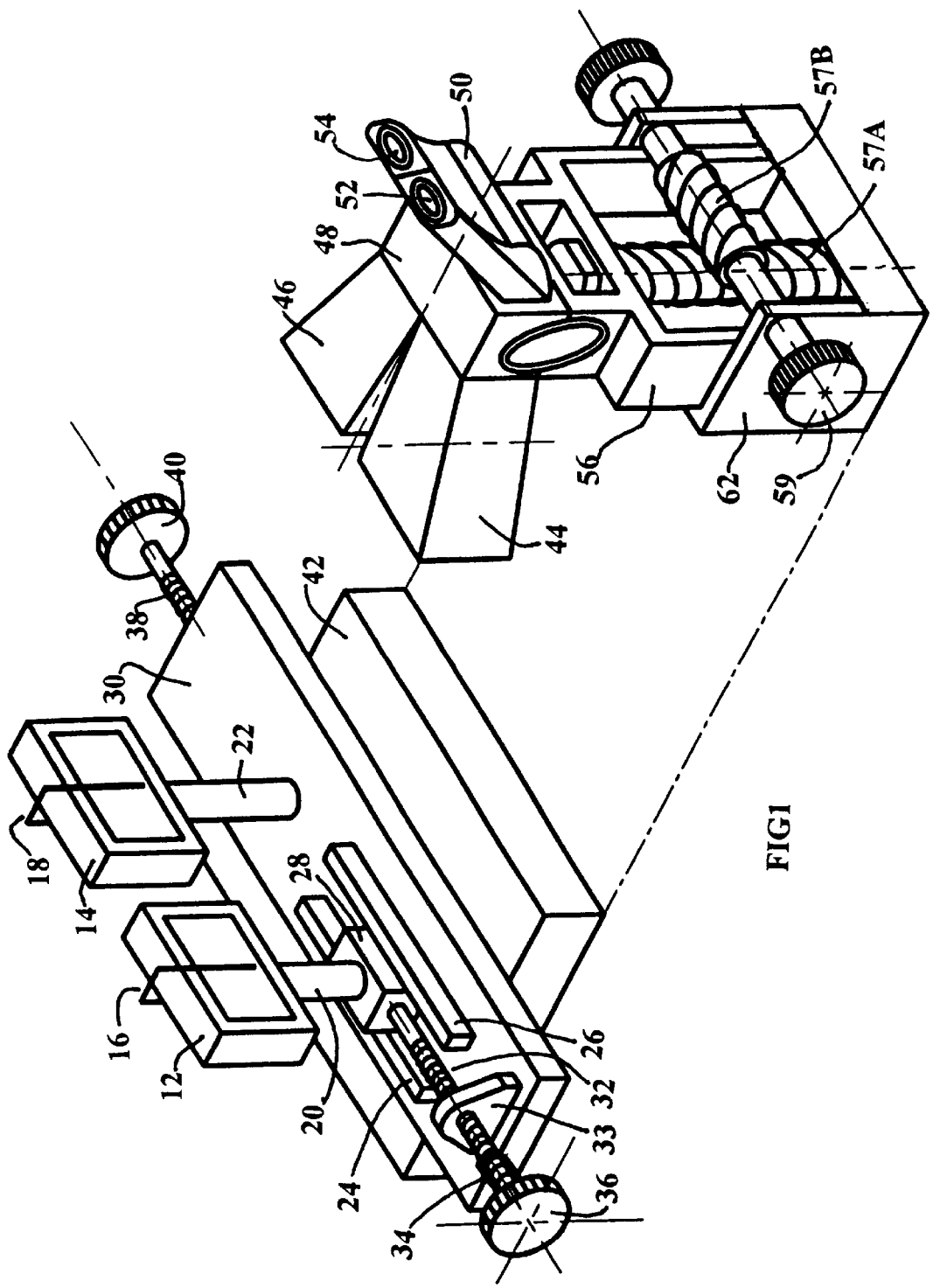
FIG. 1 Schematic showing the major components of a preferred design for a stereoscopic radiograph observing and measuring apparatus.

FIG. 1 schematically shows the major components of a preferred design for a stereoscopic radiograph observing and measuring apparatus that can be used to carry out the procedures specified in the presently invented method. Two video display devices 12, 14 are used to display a pair of radiographic images. Two reference lines 16, 18 are provided across the respective screens of the two display devices. These two reference lines may be two thin opaque wires located in front of, but very close, to the screen plane. These wires may be physically held in place by fastening means (not shown) on the apparatus base 42. These wires are not allowed to move along with the display devices 12,14 and will provide the necessary position references for measuring the image shifts and defect locations (to be explained later).

Both display devices are supported by a slidable platform 30, referred to as the primary platform, through their respective stands, 20 and 22. One of the two video display devices (shown to be the left one 12 in FIG. 1, but could have been the right one 14), through its stand 20, is positioned on a slidable platform 28, referred to as the secondary platform. The stand 20 is preferably fastened to or integrated with platform 28. Also, the stand 22 is preferably fastened to or integrated with platform 30. Platform 28 is allowed to slide horizontally between two guiding posts 24, 26 forming a trough to slidably accommodate platform 28. The sliding movement of platform 28 may be driven by any drive means. Shown in FIG. 1 is a simple driving mechanism that is constituted by a threaded shaft 32, supported by a shaft housing 33, a micrometer 34, and a turning handle 36. By turning the handle 36, one can advance or retreat the shaft screw 32 to drive the secondary platform 28 horizontally. The motion of the shaft may be either manually driven (e.g., by spinning the handle to a desired number of turns) or driven by any power tool (e.g., an electrical motor, hydraulic piston, pneumatic, solenoid, or other types of actuators). What is schematically shown in the left portion of FIG. 1 represents one of the many common sliding mechanisms that can be utilized to generate reversible sliding motions for a part. Those who are skilled in mechanical art may select from a wide array of sliding mechanisms that are commonly used and are mostly commercially available. For example, those worm shaft-worm gear combinations commonly used in moving the platforms of a milling machine or a lathe may be used for moving the secondary platform and measuring its travel distance. Similarly, a drive means, represented by 38,40 is also provided for the primary platform 30, to move the two images simultaneously. A displacement measuring means, such as a micrometer, is provided for this primary platform. The secondary platform 28 is used to horizontally shift one image with respect to the other. The two drive mechanisms need not be of same type or dimensions. The complete assembly is supported by a sturdy base 42.

The micrometers are connected in-line to measure the sliding distances of both platforms. Again, there are many simple ways of measuring the travel distance of a part. One may choose to use an optical encoder, a laser beam, or just a simple sliding caliper, etc. To use any other type of drive means or travel measuring means in the present context would merely represent a simple variation of the present invention. In a further preferred embodiment, the micrometer may be replaced by or supplemented with a displacement sensor that is capable of converting the mechanical displacement data into electrical signals in analog form. These sensors are very commonly used in the field of physical measurements. Examples include the linear variable differential transformer (LVDT) or an extensometer-type sensor commonly used in the mechanical testing of materials. Preferably, the analog signals are further converted into digital signals through an analog-to-digital (AD) converter means. These digital signals then are directly displayed in a digital display means such as a liquid crystal display. These signals may also be further used by a computer to calculate the acquired image shift distances and the spacial coordinates (X,Y,Z) of an internal feature of an object.

Figure 2:
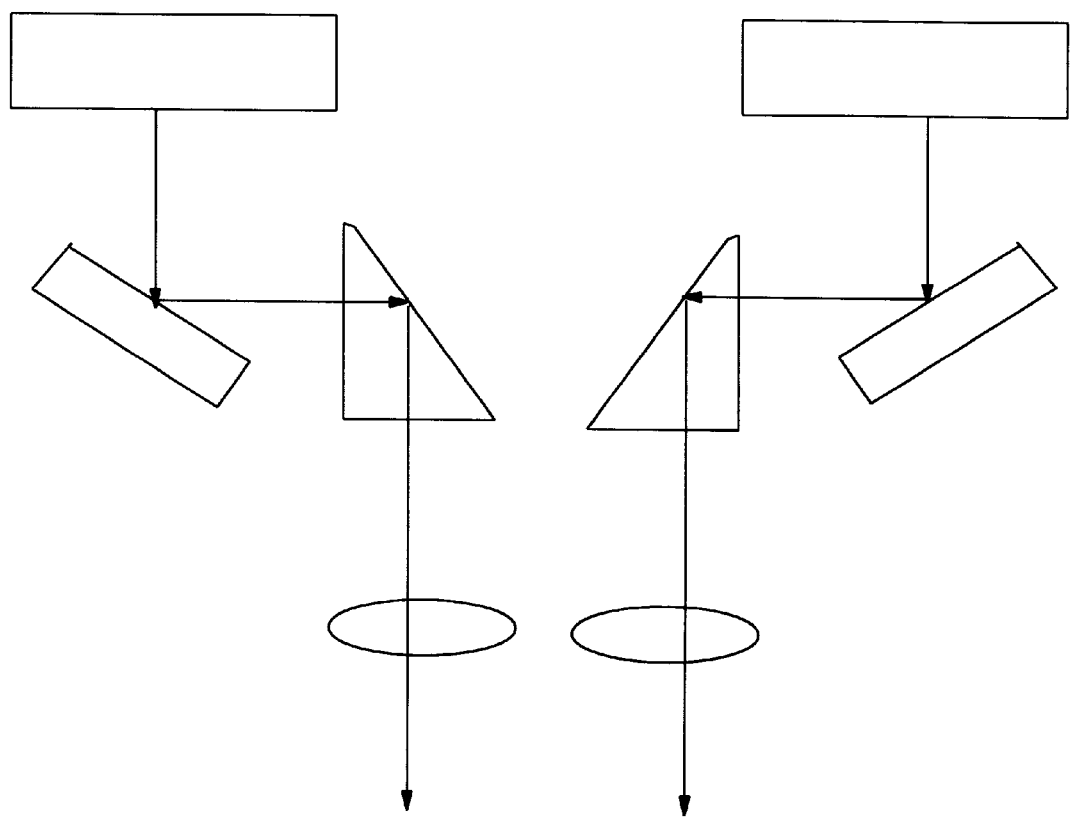
FIG. 2 Schematic showing the two optical paths in the observing compartment.

The two images shown on the screens of display devices 12,14 are to be viewed by the observing unit of the present invention, shown on the right lower portion of FIG. 1. Housed in casings 44,46,48 are mirrors and lenses that are required to direct the light from the two images to an adjustable binocular 50 including two eyepieces 52,54. This optical assembly, 44 through 54, provides two distinct and separate optical paths to meet the parallax requirement of generating a stereo perception; i.e. an image recorded from the perspective of the right eye now can be seen by the right eye while an image recorded from the perspective of the left eye seen by the left eye. The arrangement of the two optical paths is schematically shown in FIG. 2, in which the two images 70,72 are respectively reflected and re-directed through mirrors or prisms 74,78 and 76,80, and then through the lenses 82,84 in eyepieces 52,54 into the left and right eye of an observer.

The optical path assembly is supported by a stand 56, which preferably has a height-adjusting means (not shown) to move the assembly up and down as desired. Any releasable fastening means with sliding provisions, any proper ball bearing-screw combination or chain-wheel combination possibly driven by a motor means, can be set up to drive the optical assembly up and down. The stand 56 is connected to or integrated with a sturdy base 62, which can be connected to or integrated with the base 42 of the two platforms.

The operating principles for the presently invented quantitative stereoscopic radiography apparatus may be best illustrated by referring to FIGS. 3–7. Prior to taking radiographs or generating X-ray images on an image intensifier, the image orientation must be defined and reference markers established. Reference markers are set up to meet specific measurement needs. For example, in order to measure the vertical depth from the top surface of an object to an internal flaw, a small-sized lead marker may be placed on the top surface of the object. The basic procedures for carrying out radiography are shown in FIG. 3A. An imaging plate P (either a radiographic film or an image intensifying device) is placed behind the object. An image is produced on plate $P_1$ at a focal length F with the radiation source located at $S_1$. On this image plate $P_1$ are shown the image point $g_1$ of a reference marker G and the image point $a_1$ of a flaw A. The radiation source is then shifted laterally by a distance B to a new position $S_2$ while the object remains stationary. A second image is then produced on plate $P_2$ with a focal length F. This plate $P_2$ now contains the image point $g_2$ of G and the image point $a_2$ of A. Alternatively, one may choose to maintain the radiation source stationary while shifting the object laterally by a distance B (FIG. 3B). With all other parameters maintained constant, both modes of image acquisition will yield the same results.

Figure 3A:
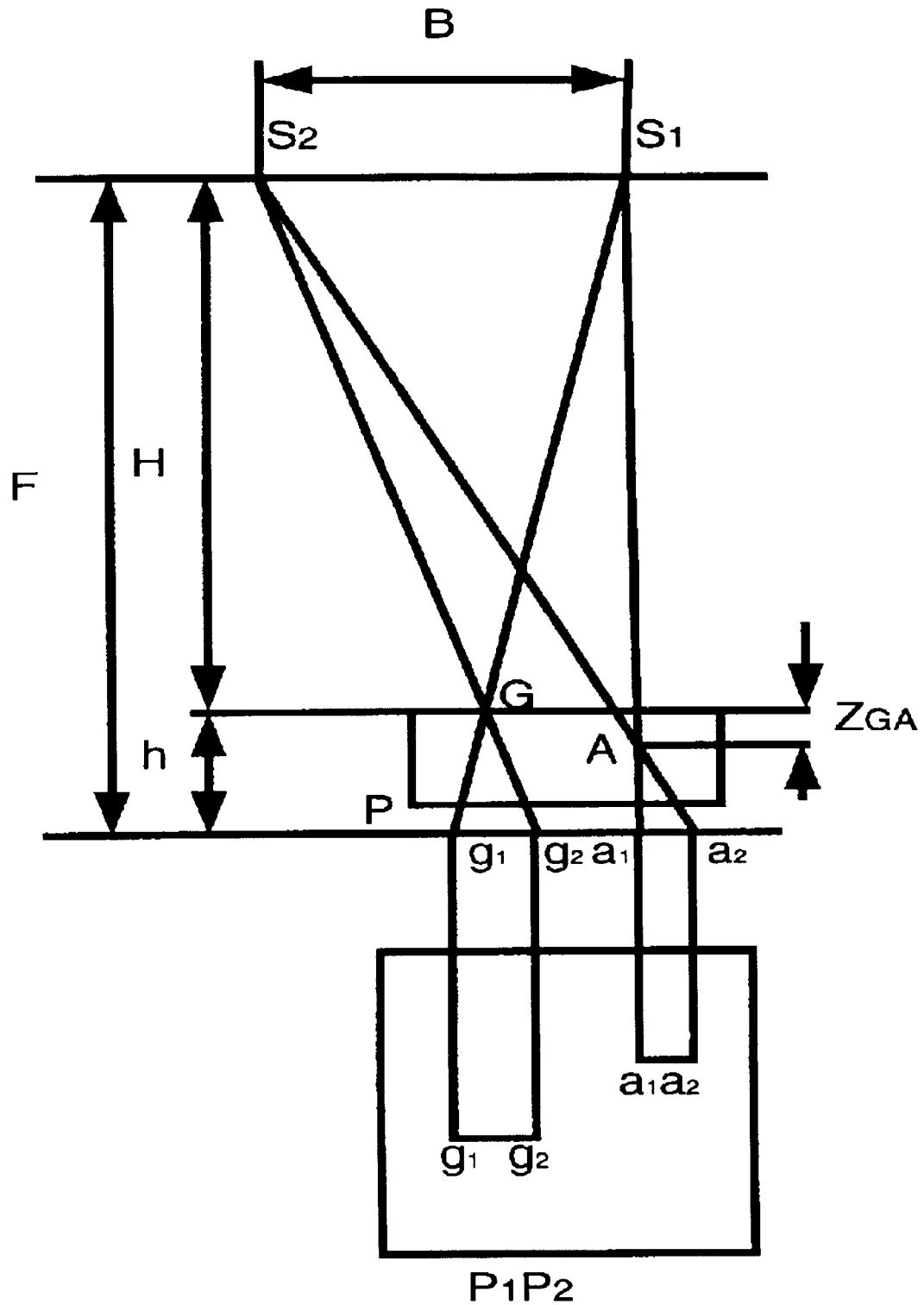
FIG. 3 (A) Geometrical relationships between a lead marker G, an internal defect A, and their images $g_1$, $g_2$ and $a_1$, $a_2$ on a radiographic film or image intensifier screen (referred to as image plane, p). An image is recorded (e.g., a radiograph $p_1$ is taken) when the X-ray source is located at $S_1$. A second image is recorded (e.g., a second radiograph $p_2$ is taken) when the source is at $S_2$. (B) The corresponding situation where the two images are taken sequentially; the second image is taken after the object is shifted laterally while keeping the X-ray source stationary.
Figure 3B:
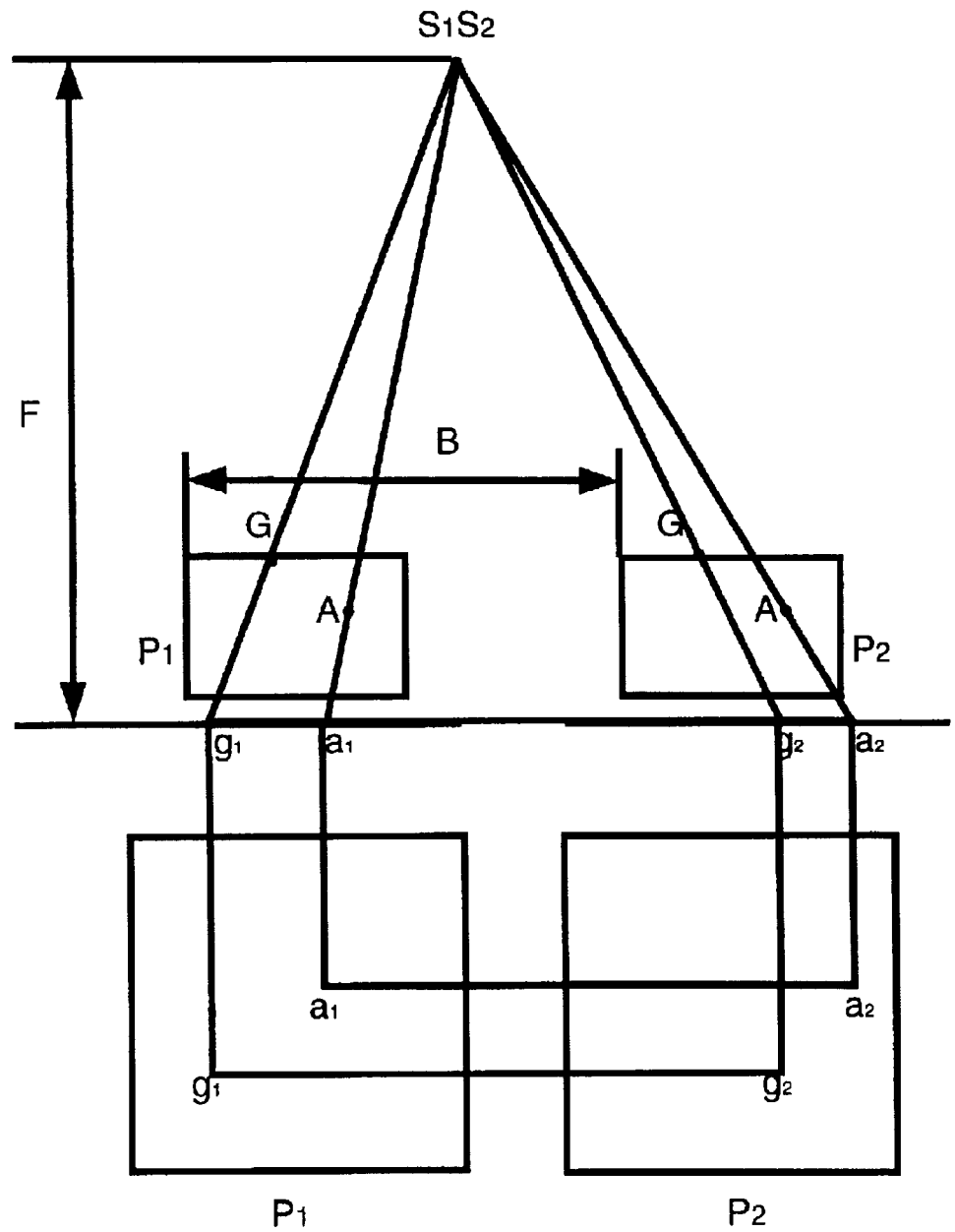
Figure 4:
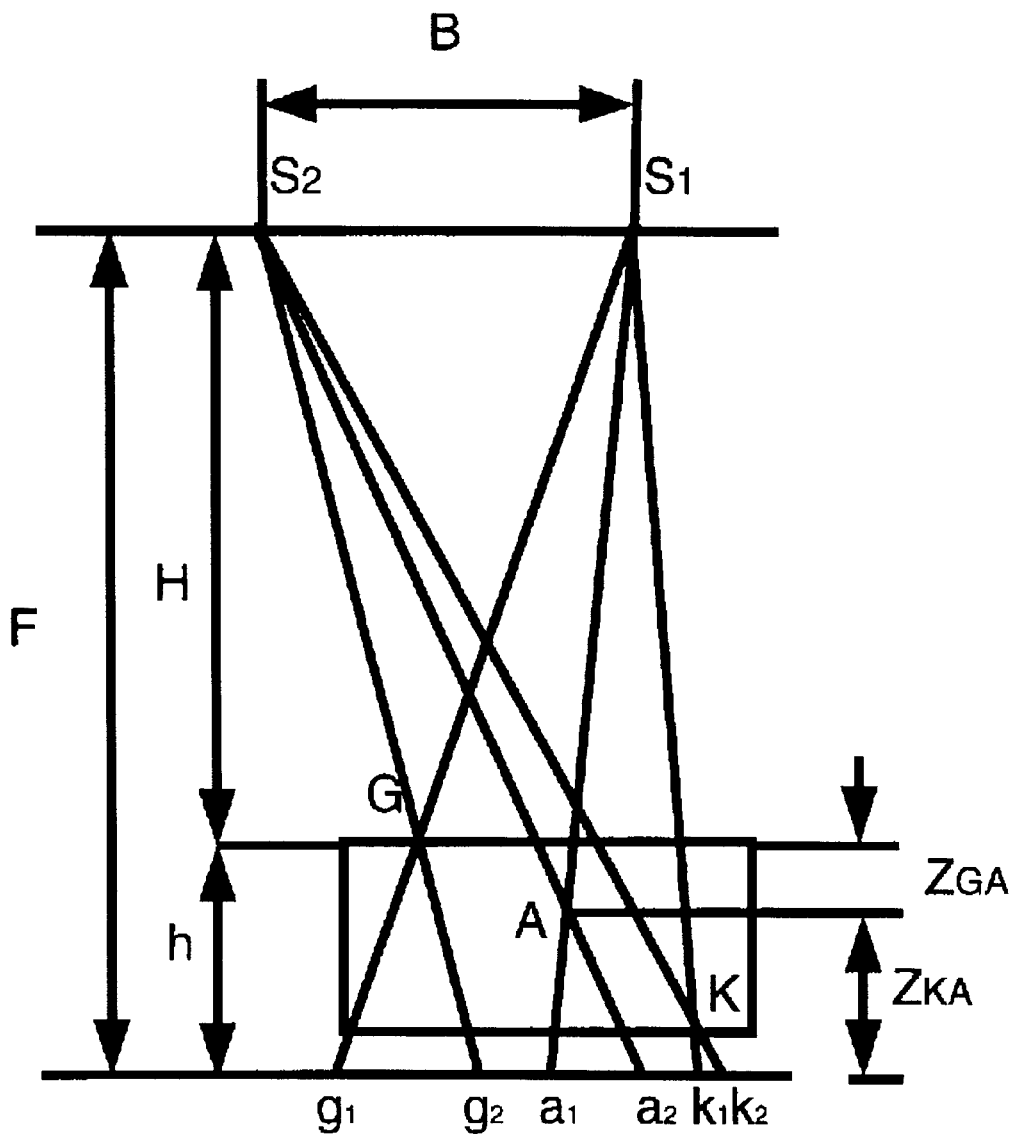
FIG. 4 Geometrical relationships between two lead markers G, K, an internal defect A, and their respective images $g_1$, $g_2$, $k_1$, $k_2$ and $a_1$, $a_2$ on a radiographic film or an image intensifier screen. This diagram helps illustrate the derivation of the formulae used in depth calculations of internal defects.

Referring to FIG. 3A, the depth from the reference marker G to flaw point A may be derived as follows: Let $Z_{GA}$ be the vertical distance from point G to point A, h the distance from the top surface of the object to the imaging plate, then H=F–h. (Related mathematical symbols are herein defined: ~ means "being similar between two triangles"; ∵ means "because"; ∴ means "therefore"; Δ, when followed by three letters, denotes a triangle; $a_1 a_2$ means the distance between $a_1$ and $a_2$)

$$\therefore \Delta S_1 A S_2 \sim \Delta a_1 A a_2$$

$$\therefore \frac{a_1 a_2}{B} = \frac{h - Z_{GA}}{H + Z_{GA}} \text{ Then } Z_{GA} = \frac{B \cdot h - a_1 a_2 \cdot h}{B + a_1 a_2} \quad (a)$$

$$\therefore \Delta S_1 G S_2 \sim \Delta g_1 G g_2$$

$$\therefore \frac{g_1 g_2}{B} = \frac{h}{H} \text{ Then } h = \frac{g_1 g_2 \cdot H}{B} \quad (b)$$

Substitution of (b) into (a) gives $$Z_{GA} = \frac{(g_1 g_2 - a_1 a_2)H}{B + a_1 a_2} = \frac{H}{B}(g_1 g_2 - a_1 a_2) \cdot \left(1 + \frac{a_1 a_2}{B}\right)^{-1} \quad (c)$$

In a normal radiographic image taking situation, $Z_{GA} \ll H$, hence $a_1 a_2 \ll B$; therefore, Eq.(c) may be simplified as:

$$Z_{GA} = H/B(g_1 g_2 - a_1 a_2) \quad (d)$$

In Eq.(d), H and B can be determined during the image taking step, $(g_1 g_2 - a_1 a_2)$ can be measured by examining the images on plates $P_1$ and $P_2$. Therefore, $Z_{GA}$ can be readily calculated provided that the apparatus permits determination of $(g_1 g_2 - a_1 a_2)$. The detailed procedure for determining $(g_1 g_2 - a_1 a_2)$ is given as follows (see FIG. 7):

Step 1: Place the images of plates $P_1$ and $P_2$ in a correct orientation according to the directional marks of the plate.

Step 2: Gently shift the primary platform 30 while observing the image from $P_2$ by right eye only until the right image point $g_2$ falls on the right reference line 18.

Step 3: Gently move the secondary platform 28 while observing the image from $P_1$ by left eye only until the left image point $g_1$ falls on the left reference line 16. Then observe by both eyes while moving the secondary platform slightly to ensure that the reference line is at the same depth as point G. At this moment, record the travel distance of the secondary platform (e.g., the reading on the micrometer is read off as $P_G$).

Step 4: Move the primary platform to bring image $a_2$ to fall on the right reference line 18.

Step 5: Move the secondary platform to bring image $a_1$ to fall on left reference line 16 (using left eye only). Observe by both eyes and move the secondary platform slightly, make sure the reference line is at the same depth as point A, and then record the travel distance of the secondary platform (the micrometer reading now shows $P_A$); Here, $P_G - P_A = \Delta P_{GA} = (g_1 g_2 - a_1 a_2)$.

In actual radiography practice, the focal length F may not be accurately measurable, resulting in some inaccuracy in defining H=F−h. Consequently, there may be a large error with $Z_{GA} = H/B \Delta P_{GA}$. In order to overcome this potential problem, one may set up another lead marker K at the bottom surface of the object. Based on FIG. 4, another depth equation for $Z_{GA}$ may be derived as follows: A simple manipulation of Eq.(b) leads to $H = Bh/g_1 g_2$ which, upon substitution into Eq.(d), gives $$Z_{GA} = \frac{h}{g_1 g_2}(g_1 g_2 - a_1 a_2) = h\left(1 - \frac{a_1 a_2}{g_1 g_2}\right)$$

$$\because a_1 a_2 = Ka_1 - Ka_2; \quad g_1 g_2 = Kg_1 - Kg_2;$$

$$\therefore Z_{GA} = h\left(1 - \frac{Ka_1 - Ka_2}{Kg_1 - Kg_2}\right)$$

Let: $Ka_1 - Ka_2 = \Delta P_{KA}$; $Kg_1 - Kg_2 = \Delta P_{KG}$

Then: $Z_{GA} = h\left(1 - \frac{\Delta P_{KA}}{\Delta P_{KG}}\right)$

Here, h is a parameter (the separation between the top surface of the object and the imaging plate) that can be measured accurately. Further, $\Delta P_{KA}$ and $\Delta P_{KG}$ are parameters that can be measured by the presently proposed apparatus. Their measurement procedures are the same as that for $\Delta P_{GA}$. Utilization of the above equations can significantly improve the accuracy for $Z_{GA}$.

Figure 5:
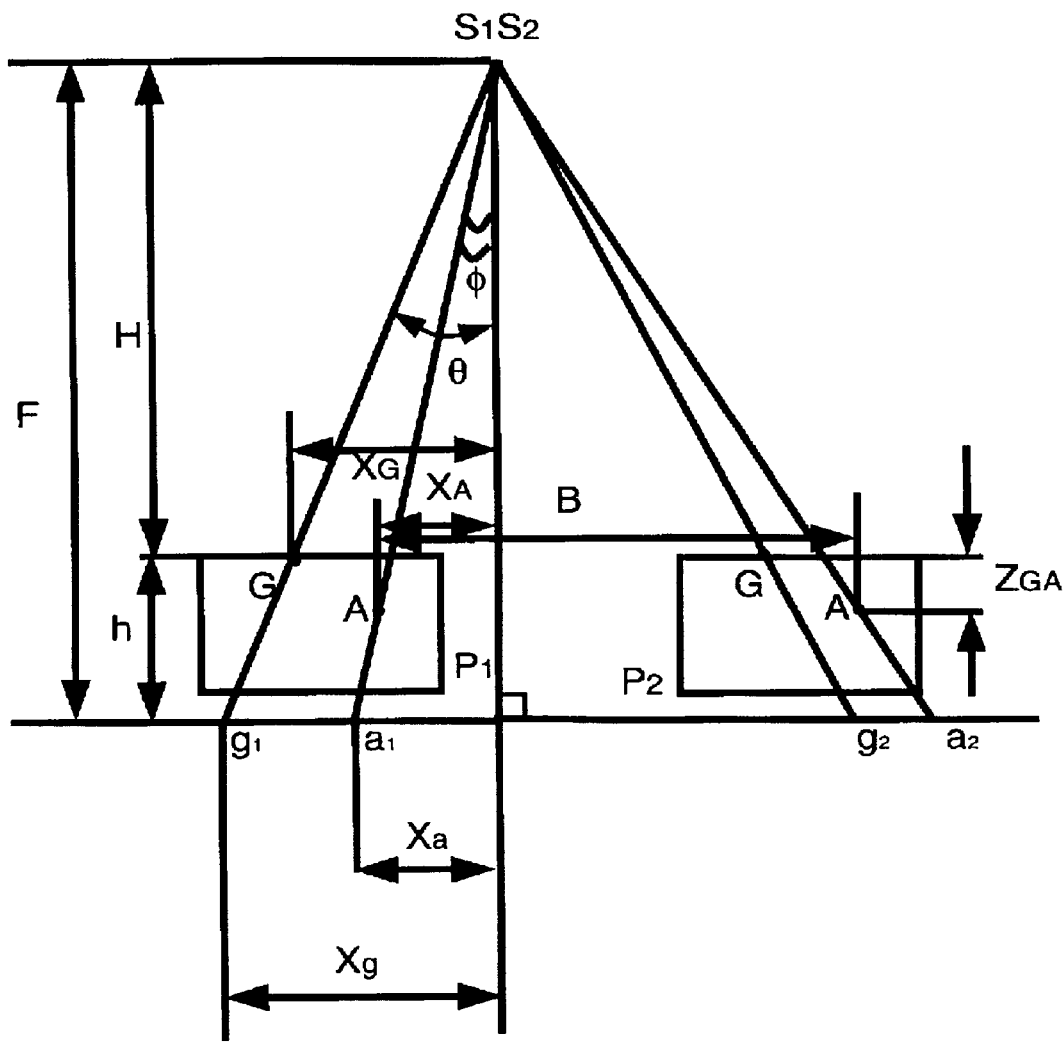
FIG. 5 Geometrical relationships between the lead marker G, an internal defect A, and their respective images $g_1$, $g_2$, and $a_1$, $a_2$ on a radiographic film or an image intensifier screen. This diagram helps illustrate the derivation of the formulae used in the calculations of horizontal image shifts or the X-coordinate value of an internal defect position.
Figure 6:
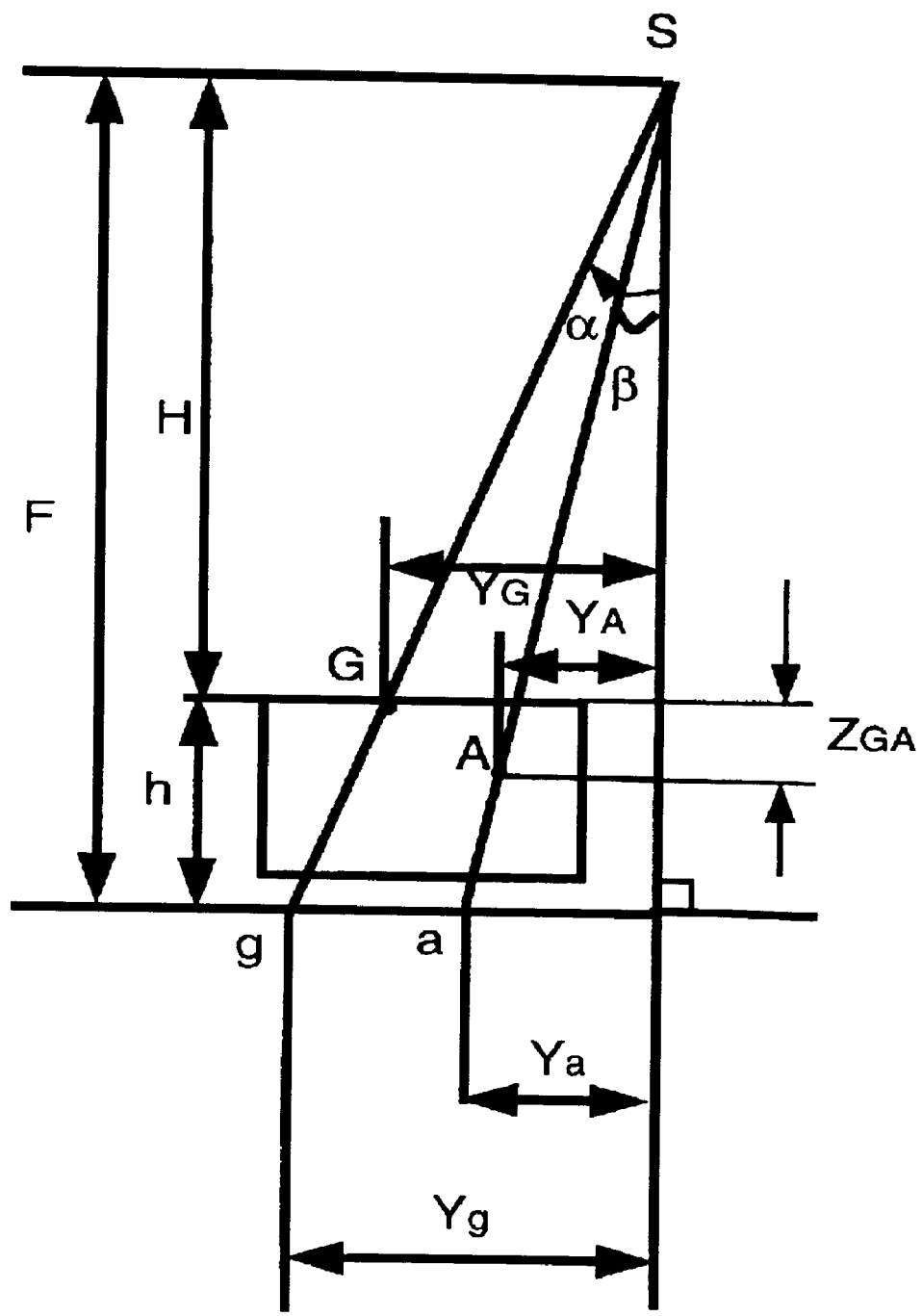
FIG. 6 Geometrical relationships between the lead marker G, an internal defect A, and their images $g_1$, $g_2$, and $a_1$, $a_2$ on a radiographic film or an image intensifier screen. This diagram helps illustrate the derivation of the formulae used in the calculations of transverse image shifts or the Y-coordinate value of an internal defect position.
Figure 7:
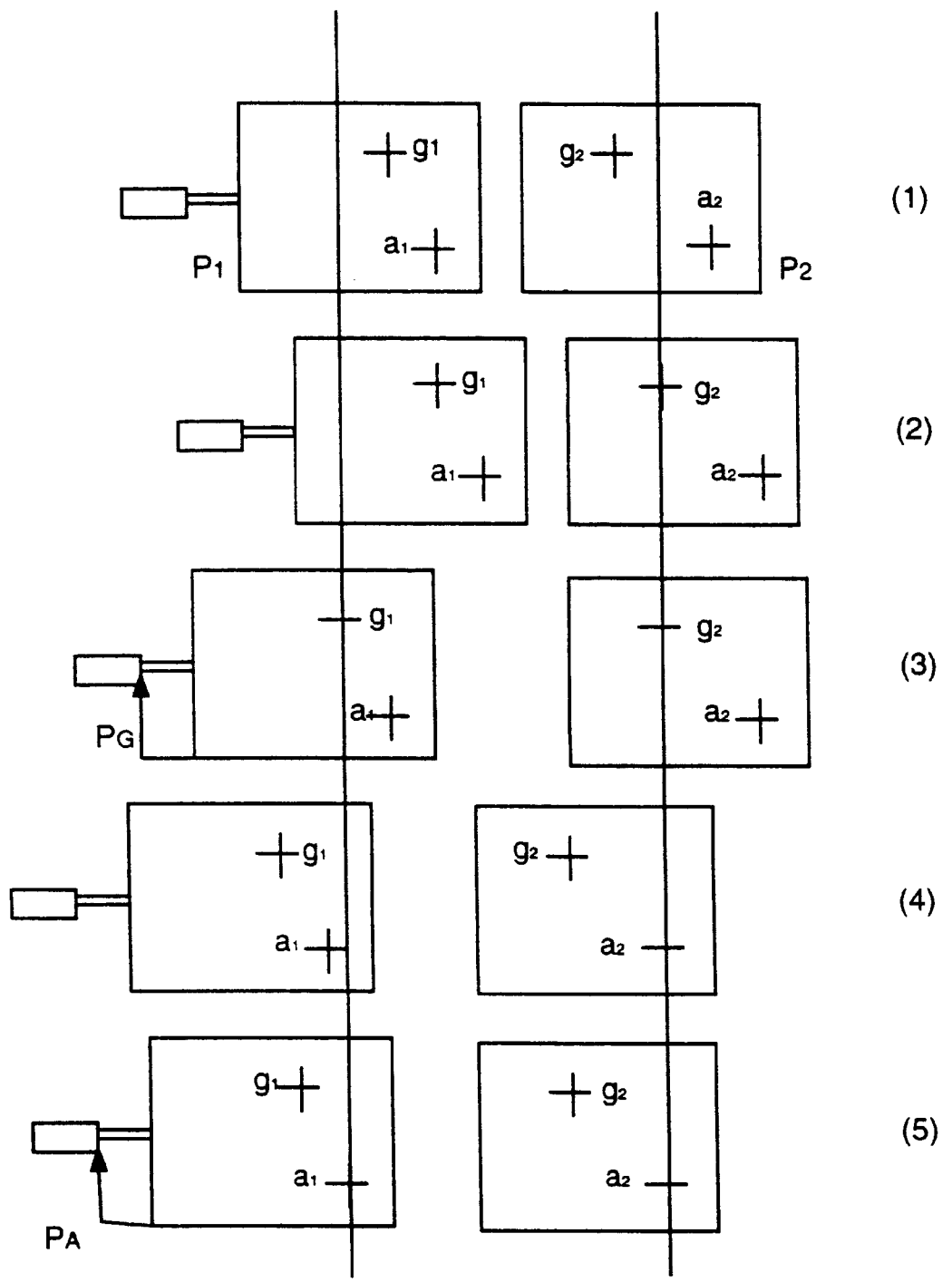
FIG. 7 Schematic showing the procedure to follow for measuring and calculating the depth of a defect.

Based on FIG. 5, the horizontal coordinate from flaw point A to reference marker point G can be derived as follows: Draw a vertical line from the radiation source $S_1, S_2$ to the plate P. Let $X_{GA}$=the horizontal distance from point G to point A; $X_A$=the distance from point A to the vertical line; $X_G$=the distance from point G to the vertical line; $X_a$=the distance from point $a_1$ to the vertical line; $X_g$=the distance from point $g_1$ to the vertical line. Then, $$\because \tan\theta = \frac{X_G}{H} = \frac{X_g}{F}$$

$$\therefore X_G = \frac{X_g \cdot H}{F}; \quad X_g = \frac{X_G \cdot F}{H}$$

$$\because \tan\phi = \frac{X_A}{H + Z_{GA}} = \frac{X_a}{F}$$

$$\therefore X_A = \frac{X_a(H + Z_{GA})}{F}; \quad X_a = \frac{F \cdot X_A}{H + Z_{GA}}$$

Also, let $\Delta Xag$ be the horizontal distance from the image point $g_1$ to image point $a_1$, then $\Delta Xag = Xg - Xa$. Substitution of the expressions for Xa and Xg into this equation leads to:

$$\Delta X_{ga} = \frac{F \cdot X_G}{H} - \frac{F \cdot X_A}{H + Z_{GA}}$$

$$\therefore X_A = \frac{(H + Z_{GA})(F \cdot X_G - H \cdot \Delta X_{ga})}{F \cdot H}$$

Since $X_{GA} = X_G - X_A$ and if the condition of $X_G = B/2$ can be met during the radiography imaging step, then $X_{GA}$ can be expressed as:

$$X_{GA} = \frac{B}{2} - \frac{(H + Z_{GA})\left(\frac{F \cdot B}{2} - H \cdot \Delta X_{ga}\right)}{F \cdot H}$$

where $\Delta X_{ga}$ is an unknown variable; however, it may be determined by examination of the image from $P_1$ with a transversely aligned ruler on the apparatus. Then, by plugging $\Delta X_{ga}$ into the equation for $X_{GA}$, one obtains the value of $X_{GA}$.

By following similar procedures, the longitudinal distance $Y_{GA}$ from the reference point G to flaw point A may be derived as follows:

$$Y_A = \frac{F \cdot Y_G(H + Z_{GA}) - H(H + Z_{GA}) \cdot \Delta Y_{ga}}{H \cdot F}$$

Deducting from both sides of the equation by the same amount $Y_G$, one obtains $$Y_{GA} = \frac{\Delta Y_{ga}(H + Z_{GA})}{F} - \frac{Y_G \cdot Z_{GA}}{H}$$

In real practice, $Z_{GA} \ll H$, therefore, $$Y_{GA} = \frac{\Delta Y_{ga}(H + Z_{GA})}{F} - \frac{Y_G \cdot Z_{GA}}{H}$$

With the present radiography apparatus, one can use a transversely aligned ruler to measure $\Delta Yga$ directly on the film $P_1$ or $P_2$ and, therefore, readily obtain the value of $Y_{GA}$.

In the equations for $X_{GA}$ and $Y_{GA}$, F and H can not be accurately measured. In order to avoid the potential error, one may obtain the values of F and H through further calculations. Referring to FIG. 4 again:

$$\because \Delta S_1 G S_2 \sim \Delta g_1 G g_2$$

$$\therefore \frac{H}{B} = \frac{h}{g_1 g_2}$$

$$\because g_1 g_2 = kg_1 - Kg_2 = \Delta P_{GK}$$

$$\therefore H = \frac{h}{\Delta P_{GK}} \cdot B; \quad F = H + h = h\left(1 + \frac{B}{\Delta P_{GK}}\right)$$

In the above equations, $\Delta P_{GK}$ can be accurately measured by the proposed apparatus, the measurement method being the same as that for $\Delta P_{GA}$ described earlier.

When viewing an object with both eyes, one sees different sides of the object from two different directions. Therefore, if a proper pair of perspective drawings, photos or other type of images corresponding to these two sides of the object are separately provided in front of their respective eyes, then the images on the retinas will provide a perception identical to what would have been visioned with both eyes. A 3-D optical model in space is thus sensed. This stereoscopic vision, obtained from viewing the preserved images, may be termed reproduction of the stereoscopic effect. The drawings, photos or images of other form producing such an effect may be termed a "photo-couple". This kind of observation with a stereoscopic effect is herein referred to as stereoscopic observation.

The above-described principle of stereoscopic observation suggests that the following conditions must be fulfilled in order to obtain reproduction of the stereoscopic effect with a photo-couple: (1) A pair of images must be taken on the same object at slightly different angles; (2) The observer must be able to use his eyes separately in viewing the images at the same time, i.e. to make each eye see only the corresponding image separately and simultaneously; (3) The photo-couple must be set up in a definitive orientation, i.e. when viewing with both eyes, the two lines of sight from the corresponding points of the photo-couple must intersect. The presently invented apparatus are designed to fulfill these conditions.

A further scrutiny on the general formulas derived above for the coordinates of feature points in space suggests that one has to measure the parallax differences of the corresponding point images. Hence, the following conditions must be further fulfilled in the design and construction of a quantitative stereoscopic radiography instrument: (4) There must be a device or a pair of devices to display a pair of images; (5) Two distinct sets of optical systems (preferably with some magnifying capability) are needed to facilitate the viewing by each eye of the respective image independently and simultaneously; (6) Adjustments must be allowed for the X- and Y-directional displacements for the image display devices and the eyepieces so that point images in various parts of the image can be seen. (7) The two images must be allowed to shift horizontally together in congruence as well as with respect to each other and there must be some devices for displacement measurements; (8) Reference lines and markers must be supplied for stereoscopic surveying. The presently invented apparatus have fully met the above-cited requirements.

Figure 8:
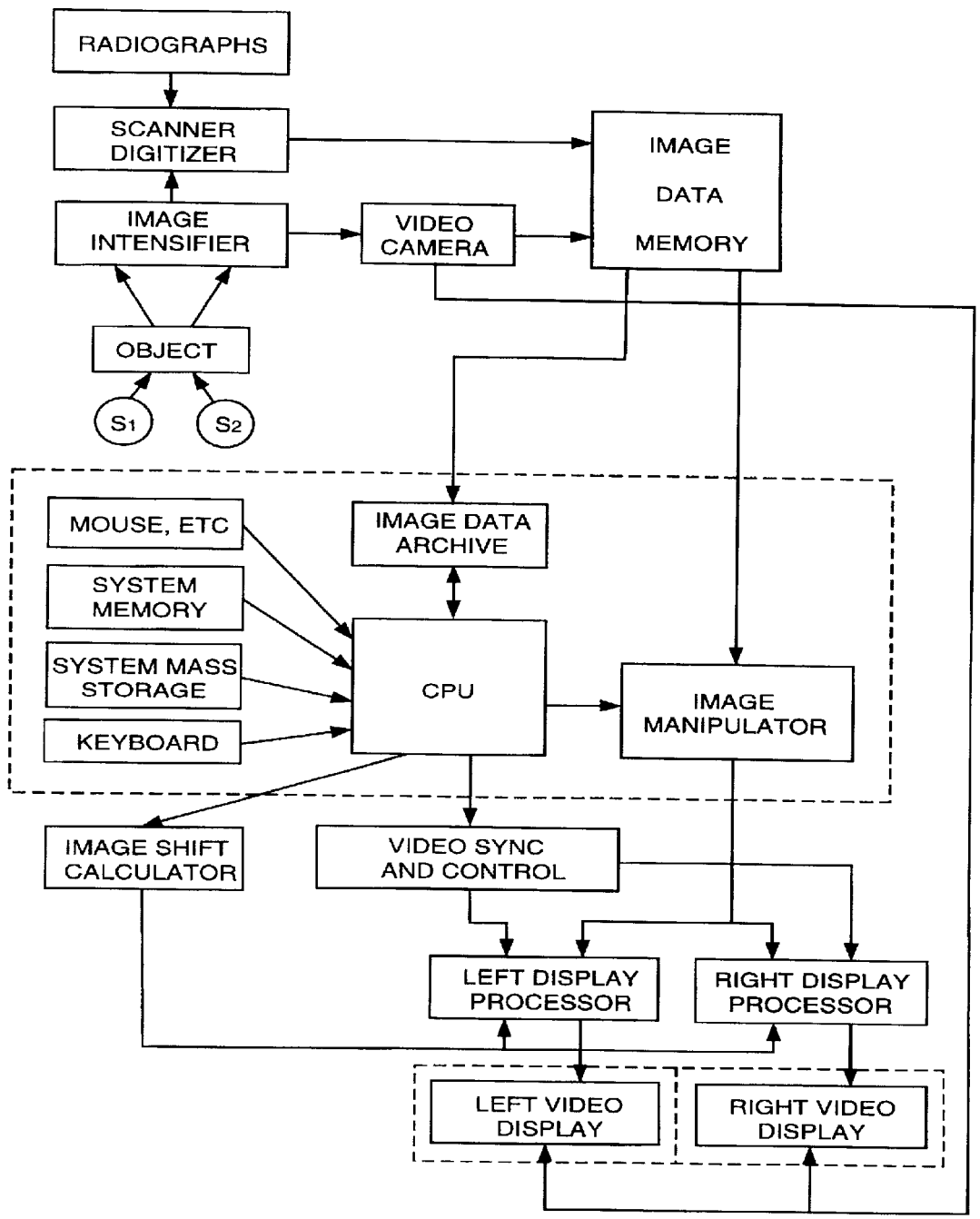
FIG. 8 A block diagram illustrating the major components and steps involved in the production and display of image pairs on video display devices.

The nature of the image display devices is further discussed herein. In its simplest form, the image plate may be just a radiographic film (negative film or transparency) or a positive print (opaque photographic paper). In the case of radiographic transparencies, a pair of film boxes with back illuminating light constitute the two required display devices. When positive prints are employed, the two display devices are simply some devices that are capable of holding a pair of prints on their flat front surfaces. When deemed necessary, the front surfaces may be illuminated with proper lighting to facilitate observation. Alternatively, referring to FIG. 8, the images in radiographs (90, negative or positive) may be stored in an image data memory 94 through a commonly used scanner or digitizer 92 for further uses later.

In fluoroscopy radiography, the images picked up by an image intensifier 96 may be recorded by a camera means 98, or other type of image sensor, and stored in the image data memory 94. Memory 94 could be either an independent memory unit or a part of the mass storage 106 of a computer 99. The system computer 99 includes a central processing unit (CPU) 100, system memory 104, system mass storage devices 106, a keyboard 108, and a screen location selection device (e.g., a mouse 102). The mass storage devices 106 may include floppy disk drives and hard disk drives for storing an operating system. These storage devices 106 also store application programs for the system computer 99 and routines for manipulating the images shown on the image display devices 12,14 and for communicating with imaging devices such as a scanner or digitizer 92, image intensifier 96, or image data memory 94.

In one embodiment of the present invention, image manipulating routines are used to drive devices such as an image manipulator 114, image shift calculator 118, video synchronization and control 116, and video display processors 120,122. Many commercially available image processing packages contain the above image manipulating and calculating capabilities. This mix of devices 114,116,118, 120,122 are needed to provide capabilities of shifting the pair of images (photo-couple) horizontally together and with respect to each other, and computing the various image shift distances required in the calculation of the coordinates of an internal flaw. In another embodiment, the two images can be shown on the screen of an image display device; only one image display device is required. These two images can be shifted together as well as shifted with respect to each other as desired. In this case, the two reference wires 16,18 will be placed near the middle of the left portion and the middle of the right portion of the screen, respectively. The two references 16,18 can be just two internally generated or externally drawn straight lines that will remain stationary when the images are being shifted.

In yet another embodiment in which a minimal image manipulating capability is needed, the sole purpose of this capability is to deliver the images to their respective image display devices 12,14. Additional image enhancing functions to improve the image quality (resolution, contrast, etc.) are nice features to have, but are not strictly required. The movements of these images are to be executed by the primary platform 30 and secondary platform 28. In still another embodiment, at least one of the two image display devices has the capability of shifting the image horizontally with reference to the other image so that the secondary platform 28 can be eliminated. In this situation, the two image display devices 12,14 are both held in place by the primary platform 30, which provides simultaneous horizontal movements of the two display devices. The two display devices are maintained at a constant separation at all times.

It is to be understood that while certain forms of the present invention have been illustrated and described herein, the invention is not to be limited to the specific forms or arrangement of the parts described and shown.

What is claimed:

1. A method of stereoscopically displaying radiographic images of the internal structure of an object and determining the spatial coordinates of a selected feature image inside said object, comprising the steps of:

(a) producing a pair of radiographic images on the same object at slightly different angles, comprising:

i. placing a high-energy radiation source to one side of said object and an unexposed radiographic film to an opposite or back side of said object so that said radiation source, object and film are aligned in a substantially straight line, ii. defining an X-Y-Z rectangular coordinate system in which the direction from the geometric center of said film to said radiation source approximately defines the Z-axis, the film width direction defines the horizontal X-axis direction, and a third axis perpendicular to both X- and Z-axes defines the transverse Y-axis direction;

iii. attaching a lead marker G to a proper position on the front surface of said object facing said radiation source so that the image of said marker can be detected by said radiographic film for the purpose of serving as an image reference point;

iv. generating a first image by irradiating a high energy radiation beam from said radiation source through said object and finally reaching said film with said marker G forming an image point $g_1$ in said first image;

v. generating a second image by replacing said exposed film with a second unexposed film, shifting said radiation source horizontally along the X-axis direction with respect to said unexposed film by a small displacement B, and exposing said second film to a radiation beam from said radiation source under a substantially identical exposure condition with said marker G leaving an image point $g_2$ in said second image;

(b) using image display devices to present said first image, referred to as the left image, to the left eye of an observer and said second image, the right image, to the right eye of said observer so that the two images can be observed by the left and right eyes separately and simultaneously; said two images being set up in a definitive orientation so that, when viewing with both eyes, the two eyes of an observer form a line being substantially parallel to the X-axis; said two images being provided with two stationary, transversely aligned reference lines, referred to as the left reference line and right reference line, respectively, across the image plane in the Y-direction;

(c) using two distinct optical paths to permit viewing of said left image by the left eye and said right image by the right eye both separately and simultaneously;

(d) performing and measuring horizontal shifting motions of said two images and obtaining the coordinate ($X_{GA}$, $Y_{GA}$, $Z_{GA}$) of an internal feature A with respect to marker G according to the following procedures:

i. Shift both images simultaneously in congruence in the X-direction while observing the right image by the right eye only until the right image point $g_2$ of marker G falls on the right reference line;

ii. Shift the left image only in the X-direction while observing the left image by the left eye only until the corresponding image point $g_1$ of said marker G falls on the left reference line and then shift one image with respect to the other in the Y-direction until the two marker image points $g_1$ and $g_2$ coincide and merge into one image point g, the two reference lines coincide to appear as one reference line, and a three-dimensional perspective of the images is developed;

iii. Observe by both eyes while horizontally shifting the left image slightly with respect to the right image until the reference line appears at the same depth as the image point g of said marker G and use displacement-metering means to measure and record a travel distance $P_G$ of the left image;

iv. Shift said two images simultaneously in congruence in the X-direction to bring an image point $a_2$ of an internal feature A of interest on said right image to fall on said right reference line;

v. Shift said left image to bring the corresponding image point $a_1$ of said feature A in said left image to fall on said left reference line while observing by using the left eye only;

vi. Observe by both eyes while shifting said left image slightly with respect to said right image until the left reference line appears at the same depth as said feature A, record this travel distance of said left image as $P_A$, and then obtain a relative image shift quantity defined as $\Delta P_{GA} = P_G - P_A$;

vii. Use the formula $Z_{GA} = (H/B)\Delta P_{GA}$ to calculate the vertical depth or Z-coordinate, $Z_{GA}$, of said feature A with respect to said marker G, where H is the vertical distance from said radiation source to said front surface of the object;

viii. Use displacement-metering means to measure the X-directional separation $\Delta X_{ga}$ between the image point g of said marker G and the image point $a_1$ of said feature A on said left image, define F to be the vertical focal length between said radiation source and said radiographic film while being exposed to said radiation beam, and then use the following formula to calculate the X-coordinate of said feature A:

$$X_{GA} = \frac{B}{2} - \frac{(H+Z_{GA})\left(\frac{F \cdot B}{2} - H \cdot \Delta X_{ga}\right)}{F \cdot H}$$

ix. Measure the Y-directional separation $\Delta Y_{ga}$ between said image point g of G and said image point $a_1$ of A on said left image, draw an imaginary vertical line from said radiation source to said radiographic film while being exposed to said radiation beam, define and measure $Y_G$ to be the Y-directional separation between G and said imaginary vertical line, and use the following formula to calculate the Y-coordinate of said feature A:

$$Y_{GA} = \frac{\Delta Y_{ga}(H+Z_{GA})}{F} - \frac{Y_G \cdot Z_{GA}}{H}.$$

2. A method of stereoscopically displaying radiographic images of the internal structure of an object and determining the spatial coordinates of a selected feature image inside said object, comprising the steps of:

(a) producing a pair of radiographic images on the same object at slightly different angles, comprising:

i. placing a high-energy radiation source to one front side of said object and an image intensifier to an opposite or back side of said object, said image intensifier being electronically connected through an image sensor to video image display means;

ii. defining an X-Y-Z rectangular coordinate system in which the direction from the geometric center of said image intensifier to said radiation source approximately defines the Z-axis, the width direction of said image intensifier defines the X-axis or horizontal direction, and a third axis being perpendicular to both X- and Z-axis defines the Y-axis or transverse direction;

iii. attaching a lead marker G to a proper position on the front surface of said object for the purpose of serving as an image reference point;

iv. generating a first image by irradiating a high energy radiation beam from said radiation source through said object and finally reaching said image intensifier, which converts said high energy radiation into visible signals which are further transferred through said image sensor to said video image display means with said marker G forming an image point $g_1$ in said first image;

v. generating a second image by shifting said radiation source horizontally along the X-axis direction with respect to said image intensifier by a small displacement B, switching on said radiation source for a second time with the radiation that penetrates said object being captured and converted to visible image signals by said image intensifier, and transferring said visible image signals to said video display means; said first image and second image being displayed side by side on said display means and said marker G leaving an image point $g_2$ in said second image;

(b) operating said video display means to present said first image, or left image, to the left eye of an observer and said second image, or right image, to the right eye of said observer so that the two images can be observed by the left and right eyes separately and simultaneously; said two images being set up in a definitive orientation so that, when being viewed with both eyes, the two eyes of the observer form a line being substantially parallel to the X-axis; said two images being provided with two stationary, transversely aligned reference lines, respectively referred to as the left reference line and right reference line, across the image plane in the Y-direction;

(c) using two distinct optical paths to permit viewing of said left image by the left eye and said right image by the right eye independently and simultaneously;

(d) performing and measuring horizontal shifting motions of said two images and obtaining the coordinates $(X_{GA}, Y_{GA}, Z_{GA})$ of an internal feature A with respect to marker G according to the following procedures:

i. Shift both images simultaneously in congruence in the X-direction while observing the right image by the right eye only until the right image point $g_2$ of marker G falls on the right reference line;

ii. Shift the left image only in the X-direction while observing the left image by the left eye only until the corresponding image point $g_1$ of said marker G falls on the left reference line and then shift one image with respect to the other in the Y-direction until the two marker image points $g_1$ and $g_2$ coincide and merge into one image point g, the two reference lines coincide to appear as one reference line, and a three-dimensional perspective of the images is developed;

iii. Observe simultaneously by both eyes while horizontally shifting the left image slightly with respect to the right image until the reference line appears at the same depth as the image point g of said marker G and use displacement-metering means to measure and record a travel distance $P_G$ of the left image;

iv. Shift said two images simultaneously in congruence in the X-direction to bring an image point $a_2$ of an internal feature A of interest on said right image to fall on said right reference line;

v. Shift said left image to bring the corresponding image point $a_1$ of said feature A in said left image to fall on said left reference line while observing by using the left eye only;

vi. Observe by both eyes while shifting said left image slightly with respect to said right image until the left reference line appears at the same depth as said feature A, record this travel distance of said left image as $P_A$, and then obtain a relative image shift quantity defined as $\Delta P_{GA} = P_G - P_A$;

vii. Use the formula $Z_{GA} = (H/B)\Delta P_{GA}$ to calculate the vertical depth or Z-coordinate, $Z_{GA}$, of said feature A with respect to said marker G, where H is the vertical distance from said radiation source to said front surface of the object;

viii. Use displacement-metering means to measure the X-directional separation $\Delta X_{ga}$ between the image point g of said marker G and the image point $a_1$ of said feature A on said left image, define F to be the vertical focal length between said radiation source and said image intensifier, and then use the following formula to calculate the X-coordinate of said feature A:

$$X_{GA} = \frac{B}{2} - \frac{(H+Z_{GA})\left(\frac{F \cdot B}{2} - H \cdot \Delta X_{ga}\right)}{F \cdot H}$$

ix. Measure the Y-directional separation $\Delta Y_{ga}$ between said image point g of G and said image point $a_1$ of A on said left right image, draw an imaginary vertical line from said radiation source to said image intensifier, define and measure $Y_G$ to be the Y-directional separation between G and said imaginary vertical line, and use the following formula to calculate the Y-coordinate of said feature A:

$$Y_{GA} = \frac{\Delta Y_{ga}(H+Z_{GA})}{F} - \frac{Y_G \cdot Z_{GA}}{H}.$$

3. A method as set forth in claim 1 in which said two images are obtained by converting said two radiographic films to two positive photographic prints.

4. A method as set forth in claim 2 in which a fluorescent screen is employed as an image intensifier to convert high-energy radiation into visible light images which are displayed on a video display device.

5. A method as set forth in claim 1 including the additional steps of (a) placing another lead marker K on the back surface of said object to produce its corresponding image points $k_1$ and $k_2$ in said left image and right image, respectively;

(b) performing and measuring horizontal shifting motions of said two images according to the following additional procedures:

i. Shift said two images simultaneously in the X-direction to bring the image point $k_2$ on said right image to fall on the right reference line;

ii. Shift said left image only to bring the corresponding image $k_1$ to fall on the left reference line while observing by using the left eye only;

iii. Observe by both eyes while shifting the left image slightly in the X-direction until the left reference line appears at the same depth as said image point $k_1$, record the travel distance of the left image as $P_k$, and then obtain a second image shift quantity defined as $\Delta P_{Gk} = P_G - P_k$;

(c) Obtain more accurate F and H values by using the following formulas: $H = hB/\Delta P_{Gk}$ and $F = h(1+B/\Delta P_{Gk})$, then follow the procedures specified in (d)-viii and (d)-ix of claim 1 to obtain more accurate values of $X_{GA}$ and $Y_{GA}$.

6. A method as set forth in claim 2 including the additional steps of (a) placing another lead marker K on the back surface of said object to produce its corresponding image points $k_1$ and $k_2$ in said left image and right image, respectively;

(b) performing and measuring horizontal shifting motions of said two images according to the following additional procedures:
  i. Shift said two images simultaneously in the X-direction to bring the image point $k_2$ on said right image to fall on the right reference line;
  ii. Shift said left image to bring the corresponding image $k_1$ to fall on the left reference line while observing by using the left eye only;
  iii. Observe by both eyes while shifting the left image slightly in the X-direction until the left reference line appears at the same depth as said image point $k_1$, record this travel distance of the left image as $P_k$, and then obtain a second image shift quantity defined as $\Delta P_{Gk}=P_G-P_k$;
(c) Obtain more accurate F and H values by using the following formulas: $H=hB/\Delta P_{Gk}$ and $F=h(1+B/\Delta P_{Gk})$, then follow the following procedures to obtain more accurate values of $X_{GA}$ and $Y_{GA}$:
  Use displacement-metering means to measure the X-directional separation $\Delta X_{ga}$ between the image point g of said marker G and the image point $a_1$ of said feature A on said left image, define F to be the vertical focal length between said radiation source and said image intensifier while being exposed to said radiation beam, and then use the following formula to calculate an X-coordinate of said feature A:

$$X_{GA} = \frac{B}{2} - \frac{(H+Z_{GA})\left(\frac{F \cdot B}{2} - H \cdot \Delta X_{ga}\right)}{F \cdot H}$$

Measure the Y-directional separation $\Delta Y_{ga}$ between said image point g of G and said image point $a_1$ of A on said left image, draw an imaginary vertical line from said radiation source to said image intensifier while being exposed to said radiation beam, define and measure $Y_G$ to be the Y-directional separation between G and said imaginary vertical line, and use the following formula to calculate a Y-coordinate of said feature A:

$$Y_{GA} = \frac{\Delta Y_{ga}(H+Z_{GA})}{F} - \frac{Y_G \cdot Z_{GA}}{H}.$$

7. A method as set forth in claim 5 in which said two images are recorded in two positive photographic prints.

8. A method as set forth in claim 4 including the additional steps of
  (a) placing another lead marker K on the back surface of said object to produce its corresponding image points $k_1$ and $k_2$ in said left image and right image, respectively;

(b) performing and measuring horizontal shifting motions of said two images according to the following additional procedures:
  i. Shift said two images simultaneously in the X-direction to bring the image point $k_2$ on said right image to fall on the right reference line;
  ii. Shift said left image to bring the corresponding image $k_1$ to fall on the left reference line while observing by using the left eye only;
  iii. Observe by both eyes while shifting the left image slightly in the X-direction until the left reference line appears at the same depth as said image point $k_1$, record this travel distance of the left image as $P_k$, and then obtain a second image shift quantity defined as $\Delta P_{Gk}=P_G-P_k$;
(c) Obtain more accurate F and H values by using the following formulas: $H=hB/\Delta P_{Gk}$ and $F=h(1+B/\Delta P_{Gk})$, then follow the following procedures to obtain more accurate values of $X_{GA}$ and $Y_{GA}$:
  Use displacement-metering means to measure the X-directional separation $\Delta X_{ga}$ between the image point g of said marker G and the image point $a_1$ of said feature A on said left image, define F to be the vertical focal length between said radiation source and said fluorescent screen, and then use the following formula to calculate the X-coordinate of said feature A:

$$X_{GA} = \frac{B}{2} - \frac{(H+Z_{GA})\left(\frac{F \cdot B}{2} - H \cdot \Delta X_{ga}\right)}{F \cdot H}$$

Measure the Y-directional separation $\Delta Y_{ga}$ between said image point g of G and said image point $a_1$ of A on said left or right image, draw an imaginary vertical line from said radiation source to said fluorescent screen while being exposed to said radiation beam, define and measure $Y_G$ to be the Y-directional separation between G and said imaginary vertical line, and use the following formula to calculate the Y-coordinate of said feature A:

$$Y_{GA} = \frac{\Delta Y_{ga}(H+Z_{GA})}{F} - \frac{Y_G \cdot Z_{GA}}{H}.$$

* * * * *